United States Patent [19]

Schenck

[11] Patent Number: 4,593,693

[45] Date of Patent: Jun. 10, 1986

[54] METHODS AND APPARATUS FOR ANASTOMOSING LIVING VESSELS

[76] Inventor: Robert R. Schenck, 1100 North Lake Shore Dr.-Apt. 33-A, Chicago, Ill. 60611

[21] Appl. No.: 727,546

[22] Filed: Apr. 26, 1985

[51] Int. Cl.$^4$ .................. A61B 17/11; A61B 17/28
[52] U.S. Cl. ................................. 128/334 R; 128/354
[58] Field of Search .............. 128/334 R, 334 C, 335, 128/303 R, 321, 322, 354

[56] References Cited

U.S. PATENT DOCUMENTS

| | | | |
|---|---|---|---|
| 2,453,056 | 11/1948 | Zack | 128/334 C |
| 2,665,692 | 1/1954 | L'Esperance | 123/334 |
| 2,733,716 | 2/1956 | Roberts | 128/321 |
| 3,048,177 | 8/1962 | Takaro | 128/334 C |
| 3,057,355 | 10/1962 | Smialowski et al. | 128/334 R |
| 3,221,746 | 12/1965 | Noble | 128/334 R |
| 3,254,650 | 6/1966 | Collito | 128/334 |
| 3,254,651 | 6/1966 | Collito | 128/334 |
| 3,279,479 | 10/1966 | Solomon | 128/321 UX |
| 3,490,455 | 1/1970 | Illig | 128/303 R |
| 3,683,926 | 8/1972 | Suzuki | 128/334 R |
| 3,774,615 | 11/1973 | Lim et al. | 128/334 C |
| 3,908,662 | 9/1975 | Razgulov et al. | 128/334 R |
| 4,366,819 | 1/1983 | Kaster | 128/334 C |
| 4,474,181 | 10/1984 | Schenck | 128/334 R |
| 4,523,592 | 6/1985 | Daniel | 128/334 C |

OTHER PUBLICATIONS

D. A. Donetskii, "A New Method For A Circular Vascular Suture", (1956 Eksperim Khirur. 1.), pp. 53–59.

Primary Examiner—Paul E. Shapiro
Attorney, Agent, or Firm—Fitch, Even, Tabin & Flannery

[57] ABSTRACT

A device for anastomosing a pair of living vessels includes a ring having at least two integrally formed hooking protrusions and an integrally formed tab by which the surgeon positions the ring. The surgeon draws an end of a first vessel through the ring and impales the wall of the vessel on the protrusions, thereby everting the first vessel. Next the surgeon hooks the second vessel wall on the protrusions to appose the intima of the vessels and anastomose the vessels. Then the surgeon detaches the tab. By using the tab to hold the ring and a forceps to manipulate the vessels, in turn, the surgeon can very rapidly join the vessels together without assistance and without approximating clamps. To aid in anastomosing vessels to a ring having outwardly-extending hooking protrusions, a microsurgical forceps is provided in which very small forked tips at the ends of the forceps. The vessel is gripped with the forceps, and the openings between the fork prongs are placed adjacent to the ends of the hooking protrusions. Then the forceps are pushed inward to impale the vessel wall with the prongs flanking the hooking protrusion. The forceps may then be slid away from the hooking protrusion, leaving the vessel wall impaled thereon.

22 Claims, 19 Drawing Figures

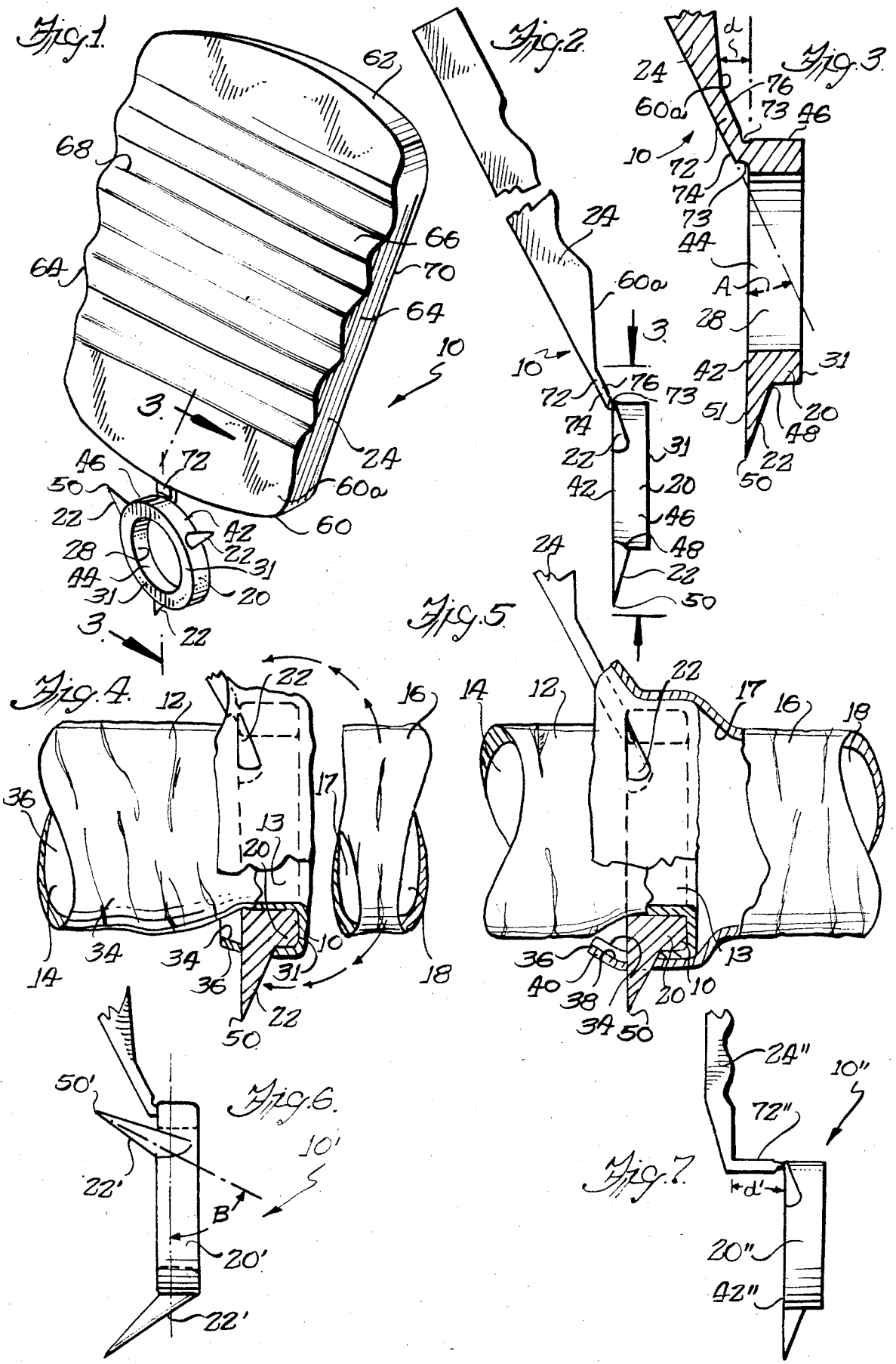

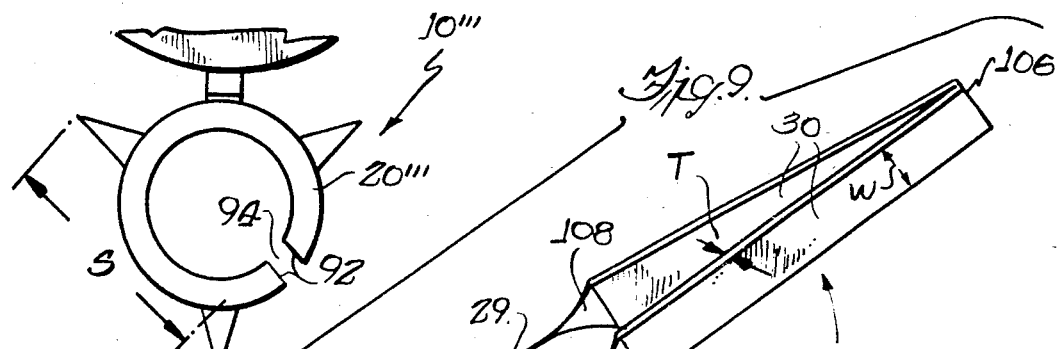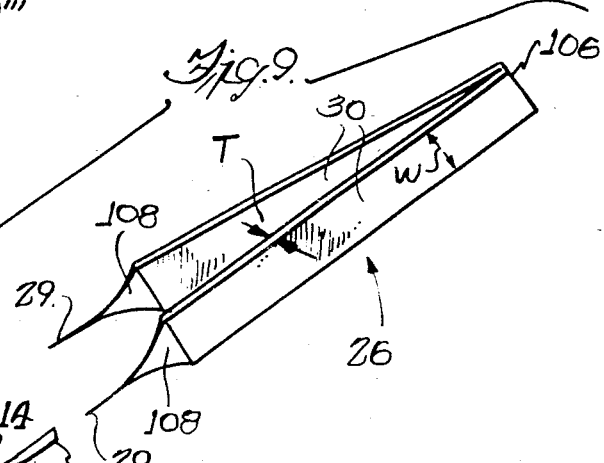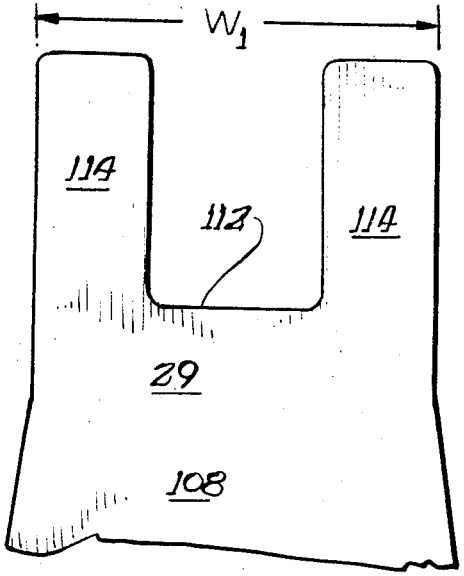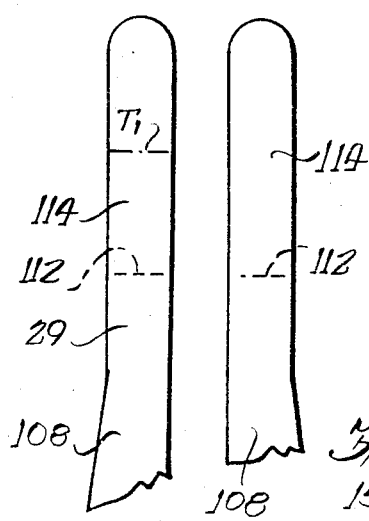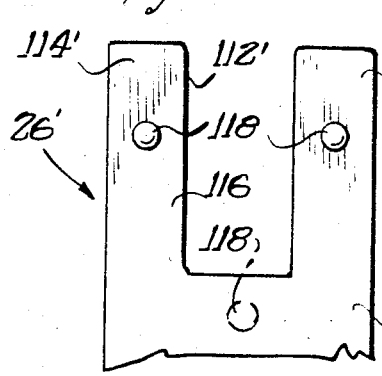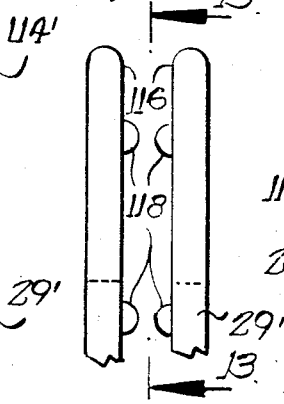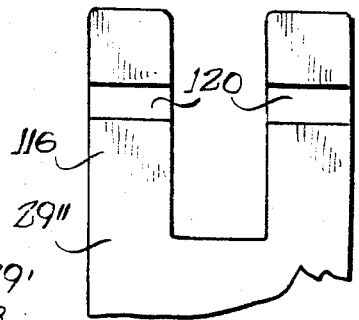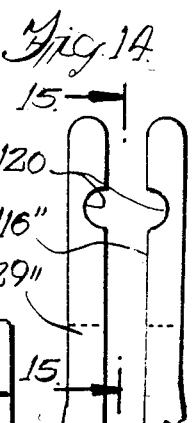

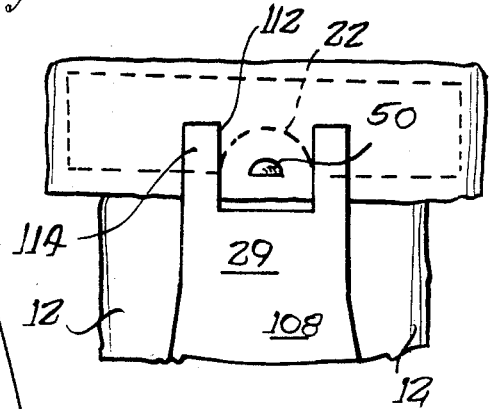
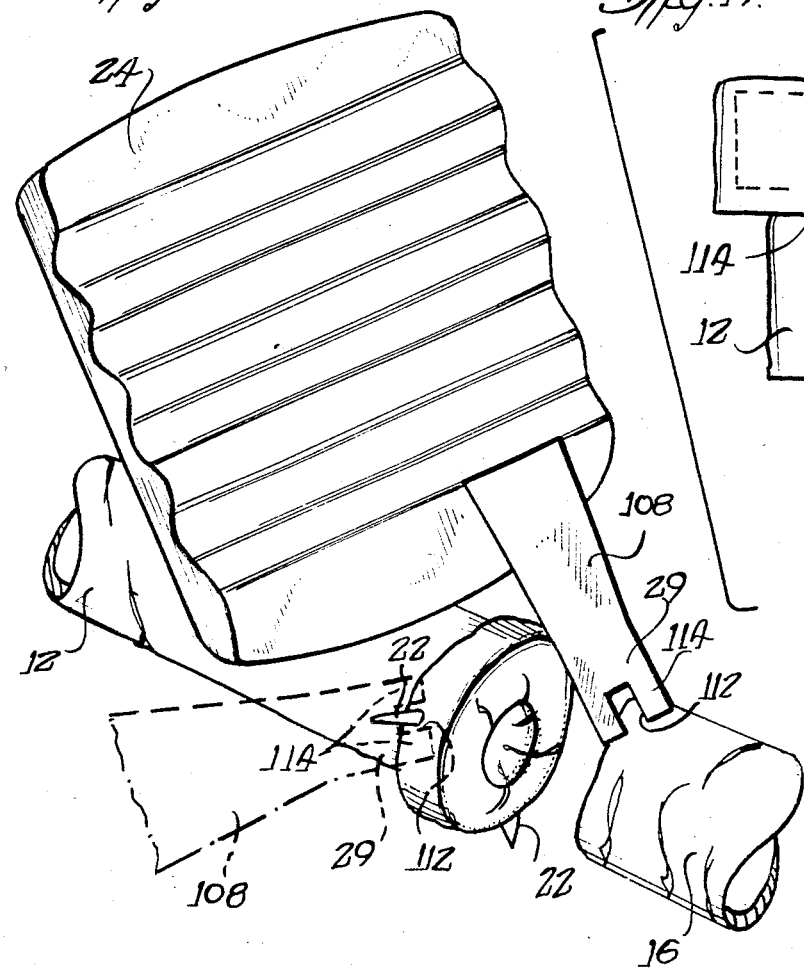
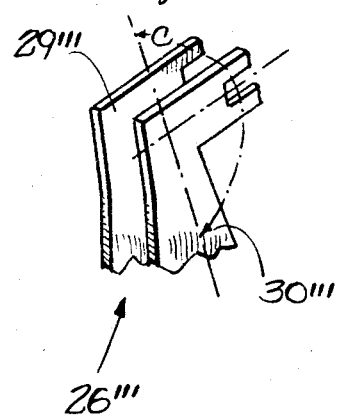
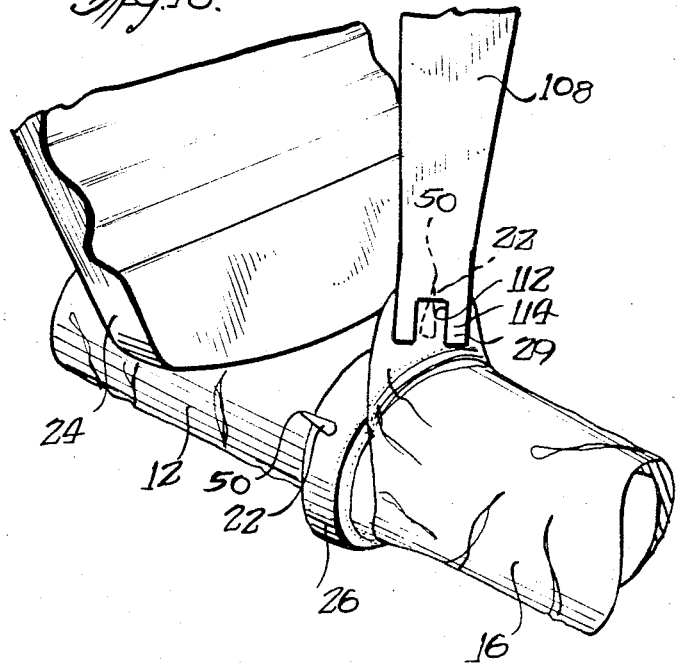

METHODS AND APPARATUS FOR ANASTOMOSING LIVING VESSELS

The present invention relates to methods and apparatus for anastomosing living vessels, particularly small living vessels, such as small blood vessels.

BACKGROUND OF THE INVENTION

Among the important and time-consuming tasks in surgical procedures is the anastomosis or joining of severed blood vessels, and the success of a surgical procedure may depend on the degree of circulation which is restored through such anastomosis. Anastomosing of living vessels is a tedious procedure, particularly in living vessels of small diameter including vessels less than 1.0 mm in diameter. Conventional suturing techniques are time-consuming, extending the duration of an operation.

To aid in anastomosing living vessels, implantable devices which connect severed ends of the blood vessel have been described previously, e.g., U.S. Pat. Nos. 3,254,650, 4,055,186, British Patent Specification No. 1,181,563, German Fed. Rep. Pat. No. 2,101,282 and Nakayama et al., Surgery, December 1962, pp. 918-931.

Even with these devices, anastomosis of small vessels takes longer than is desired. Several of the devices have multiple parts which must be joined together after the vessels have been joined to the individual parts. In most cases, joining vessels together require that the two severed ends of the vessels be held in approximating clamps that hold the vessel ends adjacent to each other for suturing or otherwise joining with the apparatus. Clamping is disadvantageous in that it is time-consuming and tedious to clamp small vessels; it is often difficult to position a clamp in the body; approximating clamps tend to damage vessel tissue; and clamping-anastomosis procedures generally require the combined efforts of at least two surgeons. Also, these prior art systems require difficult and time-consuming manipulations and operations. In many microsurgical applications, a plurality of small blood vessels must be anastomosed, and the combined time of multiple anastomoses adds to the time and expense of performing the surgical operation and reduces the chance of success.

It is a general object of the present invention to provide methods and apparatus which simplify micro-surgical anastomosis techniques, allowing a surgeon to rapidly join a pair of prepared vessels. A further object of the invention is to provide a system to allow microsurgical anastomosis without assistance and without using clamping devices that approximate the vessels.

Herein, an anastomosis ring is provided having at least two and preferably at least three protruding means for hooking the vessels to the ring and an integral tab means by which a surgeon holds and positions the ring as the vessels are being hooked to the ring, the tab means being detachable from the ring after the vessels are anastomosed. The internal diameter of the anastomosis ring is preferably equal to or slightly less than the outside diameter of the vessel, and the outside diameter of the ring is as small as is consistent with the ring having sufficient rigidity to act as the sole support of the two vessels joined thereto. To join a pair of vessels, including a first vessel end having a prepared open end and a second vessel having a prepared opening, the surgeon holds the ring by the tab and draws, e.g., with a forceps, the first vessel end through the ring. Then the surgeon draws the vessel over the end of the ring and a portion of the wall of a vessel over a protruding means so that the protruding means penetrates and hooks the vessel from the outside to the inside. The surgeon continues around the ring, similarly impaling and hooking the wall of the first vessel end on all of the protruding means until the first vessel end is securely hooked to the ring with its end everted and its intima facing outward. The observance of and the manipulation of the vessels over the ring, which is preattached to the tab, is enhanced when the tab is displaced from the plane of the ring, and the surgeon holds the ring with the tab facing the first vessel end. To complete the anastomosis, the surgeon, while using a forceps or the like to hold the ring-attached first vessel by the attached tab, draws, e.g., with a forceps, the second vessel to the ring-attached first vessel and hooks the second vessel on each of the protruding means from the inside out, thereby, apposing the intima of the vessels. The apposed vessels held by the protruding means are slightly stretched, and their natural contractive forces help to provide a fluid-tight seal between the apposed intima.

To assist in joining a pair of vessels to a ring having protruding hooking means, the invention also provides a microsurgical forceps specifically adapted for this purpose. The forceps includes a pair of tangs or arms joined at a base end and a pair of heads or tips which are proportioned to fit through the anastomosis ring and draw the first vessel therethrough. The tips each have a pair of prongs flanking a U-shaped opening, and with the tips pressed together holding a wall portion therebetween, the tips of the forceps are aligned for receiving one of the protruding means between its prongs. Then the forceps is pushed inward to impale the vessel at the location defined by the aligned U-shaped opening. Subsequently, the tips of the forceps can be slid away from the protruding hooking means, leaving the vessel wall impaled thereon.

These and other objectives and advantages of the invention will become more apparent from the following detailed description of the invention in reference to the accompanying drawings in which:

FIG. 1 is a perspective view of an anastomosis device, including an anastomosis ring and an attached tab, embodying various features of the present invention;

FIG. 2 is an enlarged side view thereof;

FIG. 3 is a further enlarged cross-sectional view taken along line 3—3 of FIG. 2;

FIG. 4 is a side view, partially cut away, of a first vessel end extended through the ring, everted around the ring and hooked onto protrusions extending from the ring;

FIG. 5 is a side view, partially cut away, of the ring in which a second vessel end is tented over the ring and over the first vessel thereon and hooked onto the protrusions;

FIG. 6 is a side view of an alternative embodiment of an anastomosis device according to the present invention;

FIG. 7 is a side view of a further alternative embodiment of an anastomosis device according to the present invention;

FIG. 8 is a front view of a still further embodiment of an anastomosis device according to the present invention;

FIG. 9 is a perspective view of forceps, embodying various features of the invention and adapted for anastomosing vessels to the device illustrated in FIG. 1, the tips of this forceps being shown greatly enlarged at the bottom of this figure;

FIG. 10 is a further enlarged front view of the tip of one of the tangs of the forceps shown in FIG. 9;

FIG. 11 is a side view of the tips of the forceps shown in FIG. 9;

FIG. 12 is a side view of an alternative embodiment of forceps tips in accordance with the invention;

FIG. 13 is a view taken along line 13—13 of FIG. 12;

FIG. 14 is a side view of a further alternative embodiment of forceps tips according to the invention;

FIG. 15 is a view taken along line 15—15 of FIG. 14;

FIG. 16 is a still further embodiment of forceps tips according to the invention;

FIG. 17 is a perspective view of a first vessel end hooked on the device of FIG. 1 and ready for attachment to the end of a second vessel, a forceps being shown in ghost attaching the first vessel to the ring and a forceps being shown in solid pulling on the second vessel preparatory to pulling the second vessel for hooking on one of the protrusions FIG. 18 is a perspective view of the forceps locating a portion of the second vessel over one of the hooking protrusions; and FIG. 19 is an elevation view of the tips of a forceps being pulled away from a vessel after the vessel has been hooked onto the anastomosis ring.

In accordance with the present invention, an anastomosis device 10 (FIG. 1) for anastomosing a first living vessel 12 (FIGS. 4 and 5) having a prepared end with a first opening 13 communicating with a first passageway 14 to a second living vessel 16 having an opening 17 communicating with a second passageway 18 includes a substantially circular ring 20, having two or more, preferably three or more, protruding or hooking means 22 for impaling and hooking the vessels and also includes attached tab means 24 by which the surgeon positions the ring during surgery but which is displaced from a plane defined by the ring so as not to interfere with hooking the vessels on the protrusions. The tab 24 is detachable from the ring 20 for removal from the body after the vessels 12,16 are anastomosed.

In accordance with a surgical method of the present invention, to anastomose a pair of vessels 12,16, a surgeon, using an instrument, such as a self-locking forceps, grasps the device 10 by the tab 24, holding the tab so that it extends in the direction of the first vessel 12. The surgeon places the ring 20 adjacent to the end of the first vessel 12 and then extends the tips 29 of tangs 30 of a microsurgical forceps 26 (FIG. 9) through the opening 28 in the ring 20, grasps a portion of the vessel wall at the end of the first vessel 12 between the tips 29 of the forceps tangs 30 and draws the first vessel end 12 through the ring. After drawing the first vessel end through the ring 20, preferably without releasing the vessel, the surgeon draws a portion of the wall of the vessel 12 over an end face 31 of the ring, and over one of the protuding hooking means 22 and then impales the vessel 12 on the protruding hooking means from its outside 34 (FIG. 4) to its everted inside or intima 36. Next, the surgeon grasps another portion of the wall of the vessel 12 and likewise impales it on another of the hooking protrusions 22. The surgeon continues this process until the end of the first vessel 12 is impaled on all of the hooking means 22. The locations at which the hooking means 22 are attached to the ring 20 are radially outward of the natural (non-expanded, non-contracted) outside diameter of the first vessel 12, and the first vessel end which is everted over the ring 20 and impaled on the hooking protrusions 22 is therefore stretched radially outward.

Next, the surgeon, gripping the tab 24 with an instrument, positions the ring 20 with the attached vessel end 12, closely adjacent to the prepared opening 17 in the second vessel 16. The surgeon grasps the second vessel, using the forceps 26 to hold a portion of the wall of the vessel between its tangs 30 and impales the second vessel wall, from its interior or intima 38 (FIG. 5) to its exterior 40, on one of the hooking protrusions 22 on which the first vessel 12 is already impaled. The surgeon then grasps the second vessel 16 at a spaced apart locations along the periphery of the opening 17 and similarly impales the second vessel wall on another hooking protrusion. The surgeon continues around the ring 20, similarly impaling the second vessel wall on successive hooking protrusions 22, until the second vessel is impaled on all of the hooking protrusions. By impaling the second vessel 16 on the circumferentially spaced hooking protrusions 22, the second vessel is stretched or tented at the opening. The natural tendency of the two vessels to contract to their unstretched states contributes to forming a fluid-tight seal between their apposed intima 36, 38. The opposed intima provide the natural environment for the fluid contained therein, e.g., blood in anastomosed blood vessels, and the apposed intima tend to heal together in a relatively short time. Once the sutureless anastomosis is complete, the surgeon detaches the tab 24, either by breaking it or by cutting it, leaving the ring 20 with the anastomosed vessels 12, 16 in the body.

The anastomosis device 10 illustrated in FIGS. 1-3 is particularly useful for joining very small vessels, such as vessels about 1 mm in outside diameter or smaller, and vessels as small as about 0.4 mm in outside diameter may be anastomosed using the devices provided by the present invention. Several factors must be considered when providing a device of this small size. The ring 20 must be formed of material that is sufficiently rigid for the ring to act as the sole support of both the vessels 12, 16 joined thereto, and the hooking protrusions 22 themselves must be sufficiently rigid to hold the stretched vessels thereto. Because of the small size of the ring 20, a practical method of providing tiny hooking protrusions 22 is by integrally forming the hooking protrusions with the ring. Preferably, the tab 24 is also integrally formed with the ring 20 and hooking protrusions. The presently preferred means of forming the integral device is by injection molding, and the device must be designed with constraints of injection molding in mind, for example, to ensure that the molding material reaches all portions of the mold cavity. As an implantable device, the material of which the device is formed must be biocompatible, and it is desirable in many instances that a material be selected which eventually dissolves or degrades within the body. Suitable materials for molding an integral anastomosis device include, but are not limited to polytetrafluoroethylene, polyglycolic acid and polylactic acid, polyglycolic acid being a presently preferred material.

Another consideration in designing the device 10 of the present invention is the anatomical function and the structural integrity of the vessel itself. For example, blood vessels must be anastomosed so as to provide good blood flow, limiting the degree to which a blood vessel may be constricted by the device. At the same time, there is a limit to the extent to which a blood vessel may be stretched without tearing, thereby limiting the outside diameter of the ring and the outward extent of the outward extremities or tips 50 of the protrusions 22. The degree to which a vessel may be stretched varies from vessel to vessel and even with respect to vessels for similar purposes. For example, the amount to which blood vessels may be stretched without tearing depends on the amount of muscle tissue associated with the walls of the blood vessel.

The ring of the integrally formed device 10 shown in FIG. 1, which represents a presently preferred embodiment of the present invention, is in the shape of an annular washer or ring having flat end surfaces 31,42, a cylindrical interior wall 44 and a cylindrical exterior wall 46. The hooking protrusions 22 in the illustrated embodiment are three semi-conical protrusions extending radially outward of the exterior wall at evenly spaced circumferential locations. The bases 48 (FIG. 2) of the protrusions 22 have thicknesses in an axial (relative to the ring) direction equal to about one half of the axial thickness of the ring and the protrusions narrow to a sharp tip or point 50. The surface 51 of each protrusions facing in the direction of the first vessel is generally continuous of the end wall 42 of the ring 20, thereby providing no slope along which the vessels 12,16 might tend to slide.

It is generally preferred to have three hooking protrusions on the ring as three evenly spaced hooking protrusions ensure that the lumen of the vessels are held open. However, other numbers of hooking protrusions may be suitable. Because the natural contraction of the vessels along the exterior surface of the ring helps to hold the vessels in place with their lumen open, in certain instances, two opposed protrusions may suffice. For larger vessels, additional protrusions, e.g., up to about 6 may be used. The less number of protrusions needed to secure the vessels, however, the less time the anastomosing procedure takes.

It is found that a ring 20 having an interior wall diameter slightly smaller than the normal or relaxed diameter of the end of the first vessel 12 which is extended therethrough and an exterior wall diameter which is slightly larger than the outside diameter of the first vessel 12 end provides the best compromise between the somewhat opposing requirements of providing as large a passageway as possible for good fluid flow and at the same time being able to stretch the vessels around the ring 20 without the walls of the vessels being torn. Accordingly, the interior wall 44 of the ring 20 is typically proportioned to have a diameter between about 0 and about 30% less than the exterior diameter of the first vessel end 12 which is to extend therethrough, while the exterior wall 46 of the ring is typically proportioned to have a diameter between about 5% to 40% greater than the exterior diameter of the first vessel end 12. The exterior diameter of the ring, therefore is between about 1.05 and about 1.7 times the interior diameter of the ring and preferably between about 1.3 and about 1.4 times the interior diameter of the ring. The thickness of the ring in an end-to-end or axial direction is generally between about one fourth and about two times the thickness of the ring in a radial direction.

The hooking protrusions 22 are intended to hold the vessels stretched while impaled thereon for the duration of the healing process. Preferably, the hooking protrusions 22 hold the vessels along a circular locus which has a diameter between about 5 to 40 percent greater than the exterior diameter of the first vessel end. The locus therefore has a diameter between about 1.05 and about 1.7 times the internal diameter of the ring and preferably between about 1.3 and about 1.4 times the internal diameter of the ring. Of course, in the embodiment of the invention illustrated in FIGS. 1-3, the outwardly extending hooking protrusions 22 hold the first vessel end 12 at their bases 48 along the exterior wall 46 of the ring 20.

The greatest degree of stretching of the vessels occurs during the hooking process, particularly after the vessel has been already impaled at one or more locations around the ring 20. It is during surgery, therefore, that the vessels 12,16 have the greatest chance of tearing. Accordingly, it is desirable to keep the ends or tips 50 of the hooking protrusions 22 as close to the radial center as possible, while at the same time ensuring that each hooking protrusions has sufficient length to impale both vessels stretched thereover. For hooking a pair of vessels 12,16 in the range of about 1 mm in size or less, it is generally necessary that the length of each hooking protrusion from its base 48 to its tip 50 be at least about 0.3 mm. At the same time, it is preferred that the tips 50 of the hooking protrusions 22 extend along a circular locus that has a diameter which is between about 1.5 to about 2.0 times the external diameter of the first living vessel end. Thus for a ring having an exterior diameter between about 5 to 40% greater than the external diameter of the first vessel end, the circular locus along which the tips 50 of the hooking means lie will have a diameter between about 1.8 and about 2.6 times the interior diameter of the ring and preferably between about 2.0 and about 2.4 times the interior diameter of the ring.

An important concern in proportioning the ring is that the vessel is not torn during anastomosis because of the necessity of stretching the vessel. It is to be appreciated that the end of the vessel is cut and has a tendency to tear from its end inward. Also, the vessel is being punctured at points near its cut end, and due to the stretched nature of the vessel during anastomosis, there is a tendency to tear from the puncture points. The most critical juncture at which tearing is likely to occur is when a vessel is hooked on one of the protuberances 22 lying along the base of the protuberance and is being hooked over the tip 50 of the adjacent protuberance because it is here that maximum stretching occurs. At this juncture, the stress on the tissue is along a line between the base of one protuberance and the tip of an adjacent protuberance. This distance "S" is illustrated in respect to the alternative embodiment shown in FIG. 8, and is from the midpoint of the base of one of the protrusions to the tip of the adjacent protrusion. It is this distance "S" which is desirably minimized. If the vessels are to be impaled on a ring with three evenly spaced protrusions, to avoid undue stretching, the distance "S" will be between about 1.4 and about 1.7 times the external diameter of the first vessel end, or between about 1.4 and about 2.3 times the interior diameter of the ring, which will result in the tissue that is stretched between the base of one protrusion and the tip of another being expanded between about one and one-half and about two and one-half times its normal state. The distance "S" which is permissable will change if a different number of evenly spaced hooking protrusions are provided on the ring; however, in any case, the ring and the protrusions should be proportioned so that the tissue is temporarily stretched to no more than about one and one-half to about two and one-half times its normal state. In order that the distance "S" not be excessive, generally for a ring adapted for anastomosing a vessel 1.0 mm in diameter or smaller, the protrusions will extend no more than about 0.5 mm from base to tip, and preferably no more than about 0.4 mm from base to tip. In rings for anastomosing larger vessels; however, the protrusions may be proportionately longer. It should also be appreciated that the permissible degree of stretching will depend on the strength of the particular vessel itself, and a vessel strengthened with substantial amounts of associated muscle tissue might be stretched a greater distance. After impaling the vessel on each protrusion, the vessel is drawn inward along the protrusions, to along the exterior of the ring, whereat the degree of stretching is no longer an important concern.

An important aspect of the present invention is the tab 24 which is pre-attached to the ring to enable the surgeon to hold and position the ring, and with the aid of a forceps 26 perform the anastomosis of a pair of vessels as an unassisted one-surgeon operation in a very short time. The anastomosis may, of course, be assisted by a second physician, and in any case the tab facilitates positioning the ring. The shape of the tab 24 is not considered particularly important, but should facilitate gripping by the surgeon's instrument without being overly large. The tab 24 illustrated in FIG. 1 is adapted to be gripped by an instrument that is held between two digits of the surgeon's hand, e.g., between his thumb and forefinger and is approximately 3 mm by 4 mm. A suitable instrument for gripping the tab is a self-locking forceps, such as that sold by Springer & Tritt, Unit No. CAF-4C. The front edge 60 and rear edge 62 are each curved and the lateral side edges 64 are generally straight and parallel. To provide a better grip for the instrument, one broad surface 66, in this case the surface facing away from the first vessel end 12 during surgery, is formed with ridges 68 which interfits with the tips of the above-mentioned forceps. It is to be understood that other uneven surfaces may be used for gripping with other forceps or similar instruments. Also, gripping surfaces might be formed on both broad surfaces. In this illustrated case; however, the broad surface 70 facing the first vessel end 12 is smooth.

The manipulation of the ring 20 is done by a surgeon while viewing the vessels under a microscope and while using the forceps 26. A visual line of sight problem occurs. It has been found that surgeon's line of sight and view is less obstructed if the tab 24 is displaced from the plane of the ring. In the embodiment of the device 10 shown in FIGS. 1–3, the tab 24 is displaced from the plane of the ring by forming the tab at an angle A (FIG. 3) relative to the ring, in this case about 30°. The angle may vary, however, from about 5° to about 45°. The front edge surface 60a is chamfered relative to the broad tab surfaces 66, 70 so as to be generally parallel to the plane of the ring, and this inner edge surface, which represents the closest surface of the tab to the ring, is displaced axially from the ring by a distance "d" (FIG. 3) at least about one-half of the ring's axial thickness.

It is generally necessary to remove the tab 24 from the ring 20 subsequent to vessel anastomosis, and to facilitate detachment of the tab from the ring after the vessels 12, 16 have been anastomosed, the tab is joined to the ring by a narrow neck 72 which may be broken or cut from the ring after surgery. The neck 72 is quite narrow relative to the tab 24 both in thickness and in width. The neck in FIG. 1 is formed to extend from the end face 42 of the ring that faces the first vessel end 12 and has one surface 74 continuous with the flat broad surface 70 of the tab and an opposite parallel surface 76 which intersects with the front edge surface 60a of the tab. The neck 72 is preferably located along the ring 20 midway between two of the hooking protrusions 22 so as to minimize its interference with hooking the vessels on the protrusions. Thus, in the case of a ring 20 having three hooking protrusions 22, the neck 72 is disposed diametrically opposite one of the hooking protrusions and about 60° along the circumference of the ring from each of the others.

To further facilitate breaking of the tab 24 from the ring 20, the neck 72 is notched or scored 73 along its intersection with the ring. The notch 73 may be formed during the molding process or may be formed by scoring with an instrument, such as a surgical scalpal, after the device 10 is molded. The notch is optional, and instead of breaking the neck from the ring after anastomosis, the thin neck may be easily cut, for example, with sissors.

A typical ring 20, structured as described in reference to the FIG. 1–3 embodiment and adapted for suturing a 1 mm outside diameter vessel, is proportioned as follows. The ring has a 0.76 mm internal diameter, a 1.06 mm external diameter and an end face to end face (axial direction) thickness of 0.1 mm. Three protrusions 22 each extend 0.4 mm outward of the external wall of the ring. The tab 24 is 2.8 mm wide (between its lateral edges), 3.6 mm long and about 0.38 mm thick. The interconnecting neck 72 is 0.3 mm wide, 0.3 mm long and 0.15 mm thick.

Illustrated in FIG. 6 is an alternative embodiment of a device 10' according to the present invention. In this case, the axes of the hooking protrusions 22' are angled relative to the plane of the ring 20' (or to the radial direction) at an angle B up to about 60° in the direction of the first vessel end 12. Angling of the protrusions 22' enables a sufficiently long protrusion to be provided while reducing the diameter of the locus of the tips 50' of the protrusions. Furthermore, once the vessels are hooked, the angle of the protrusions 22' opposes any tendency of the impaled vessels to pull away from the ring 20'. It is found; however, that angling of the protrusions 22' makes it somewhat more difficult to anastomose vessels together than with a ring having protrusions with axes extending radially outward, i.e., with axes in the plane of the ring.

Illustrated in FIG. 7 is another alternative embodiment of a device 10" according to the present invention. In this case, the tab 24" is displaced from the plane of the ring 20" by a neck 72" which extends perpendicularly from one end face 42" of the ring, and the tab 24" is also formed perpendicular to the ring and in a plane substantially parallel to the plane of the ring. The displacement of the tab from the ring "d'" is at least about one half the axial thickness of the ring and preferably at least about one ring thickness. This configuration has advantages in that the direction by which the surgeon moves the tab 24" is the direction which the ring 20" is moved.

Illustrated in FIG. 8 is a still further embodiment of a device 10'" according to the present invention. In this embodiment, the ring 20'" is substantially, but not completely encircling, having spaced-apart ends 92 defining a gap 94 therebetween. Certain vessels in the body are attached by connective tissue to other organs, examples being the fallopian tubes and vas deferens. The gap 94 in the ring 20'" accommodates this connective tissue, allowing the ring to substantially encircle the vessel without the connective tissue being cut from the supporting organ. The gap 94 may either be formed in the molding process or may be cut into the ring, e.g., with a laser, subsequent to ring formation.

In accordance with a further aspect of the present invention, microsurgical forceps 26 (FIG. 9) are provided which are particularly suitable for suturing with an anastomosis ring 20 having hooking protrusions 22. The forceps 26 comprise a pair of resiliently deformable, e.g., spring metal, tangs or arms 30 joined together at a base end 106 in a conventional manner so that the arms are naturally biased to an open position. The arms 30 have a sufficient maximum width "W" in a gripping portion to facilitate gripping and manipulation by the surgeon, and a sufficient maximum thickness "T" for providing the necessary resilient deformability to the tangs. Generally, the maximum width W is at least about 7 mm and the maximum thickness T is at least about 1 mm. Connected to the main part of each arm 30, by means of a narrowing neck portion 108, is a head or tip 29 particularly designed for placing a vessel 12 or 16 over a ring 20 with outwardly extending hooking protrusions 22. Each of the opposed tips 29 is very small in order to enable the tip to be extended through the opening 28 in the ring 20, grasp a wall of the vessel end 12 and used to draw the vessel end through the opening in the ring. Indeed, the tips 29 are so small that the configuration thereof can barely, if at all, be ascertained without magnification thereof which, of course, is done in actual use when the surgeon is using a microscope. The maximum width ($W_1$) of each tip 29 is very small compared to the maximum width (W) of the tang 30, being at least about 15 times smaller and typically up to about 100 times smaller. The maximum thickness ($T_1$) of the tip 29 is likewise small compared to the maximum thickness (T) of the tang 30, being at least about 10 times smaller than the maximum thickness T of the tang and typically up to about 50 times smaller. The maximum width $W_1$ of each tip is generally less than about 0.5 mm and the maximum thickness $T_1$ of each tip is generally less than about 0.1 mm. Formed into the very small head 29 is a generally U-shaped opening 112, defining a forked or bifurcated tip defined by two flanking prongs 114 at the end of the tip. The opening 112 is proportioned to receive one of the hooking protrusions 22 of the ring therethrough.

In anastomosing a pair of vessels using a ring 20 with hooking protrusions 22 and a forceps 26 having opposed forked tips 29, each with the two prongs 114, the surgeon positions the ring adjacent to the ends of the first vessel 12, inserts the tips 29 of the forceps 26 through the ring opening 28 and grasps the end of the vessel 12 by a portion of its wall so that one forceps tip is against the inside or intima 36 of the vessel wall and the other tip is against the outside 34 of the wall. Then, the surgeon draws the first vessel 12 end through the ring 20. Next, the surgeon draws the vessel end radially outward over the tip 50 of a hooking protrusion 22 and impales the vessel by pushing inward with the forceps 26 so that the protrusion 22 extends through the aligned U-shaped openings 112 with the fork prongs 114 flanking the protrusion. Once impaled, the surgeon merely slides the forceps 26 away from the protrusion 22, leaving the vessel 12 impaled on the hooking protrusion as best seen in FIG. 19.

The process continues as described above with the vessel being impaled on each protrusion by locating the aligned U-shaped opening 112 of the forceps 26 at the tips 50 of the hooking protrusions 22 and pressing the forceps 26 inward. Shown in ghost is FIG. 17 is the tip 29 of the forceps 26 having completed attachment of the first vessel end 12 to the ring (which is covered by the everted first vessel end) with its prongs 114 extending along one of the hooking protrusions 22. Shown in solid in FIG. 17 is the tip 29 of the forceps 26 grasping the end of the second vessel 16 and pulling it outward for penetration by one of the hooking protrusion 22, and shown in FIG. 18 is a view of the forceps tip 29 locating a portion of the wall of the second vessel 16 over one of the hooking protrusions. The second vessel is impaled in a similar manner. The microsurgical forceps tips 29 facilitate anastomosing with this type of anastomosis ring 20 by helping to locate the exact location of the vessel which is to be impaled at the tips 50 of the protrusions 22 and then helping to apply the force necessary to impale the vessels walls precisely at these locations.

Illustrated in FIGS. 12 and 13 is a further embodiment of the microsurgical forceps 26'. In this case, the facing surfaces 116 of the heads or tips 29' have small bumps 118 or protrusions which provide an improved grip on the vessel. Each of the illustrated forceps tips 29' has three protrusions 118, one toward the end of each prong 114', and one just inward of the U-shaped openings 112'.

Illustrated in FIGS. 14 and 15 is a further embodiment of surgical forceps 26''. In this case a groove 120 in the facing surfaces 116'' of each of the tips 29'' facilitates, gripping of the vessels.

In the embodiment of the forceps 26 shown in FIG. 9, the axis of each tip 29 and the U-shaped opening 112 is colinear with the axis of the tang 30. Also provided is a microsurgical forceps 26''' with tips 29''' that are at an angle "C" relative to the axis of the tangs 30''' by up to about 90°, as shown in FIG. 16, which forceps may better enable the surgeon to position the tips in certain surgical applications.

The invention will now be illustrated by way of specific example.

EXAMPLE

A male Sprague-Dawley rat weighing 230 grams was anesthetized with intraperitoneal pentobarbital, and the cartoid artery was exposed. The external vessel diameter was about 1.0 mm measured prior to arterial isolation to avoid diameter variation induced by spasm or dilation due to smooth muscle relaxation by topical lidocaine.

A suture ring with an attached tab, as shown and described with reference to FIGS. 1-3, was used to rejoin the severed artery. The ring had the dimensions described above for suturing a vessel 1.0 mm in diameter. Also used in the anastomosis was a forceps 26, substantially shown and described in FIG. 9, in which the tip 29 on each tang 30 was 0.35 mm wide, 0.10 mm thick and had a U-shaped opening 0.015 mm wide and 0.40 mm deep. The forceps was used to draw the end of the first vessel through the opening in the ring 20, evert the vessel 12 and impale the vessel end on each of the three protrusions 22. Then with the surgeon still holding the suture ring by its tab, the other end of the vessel 16 was similarly grasped with the forceps and impaled on the protrusions so as to appose the intima of the ends of the vessels and effect a fluid-tight anastomosis. The entire anastomosis procedure was performed in about one minute, an extremely short time for this type of procedure. The anastomosis proved to be patent, i.e., it remained open to the flow of blood therethrough.

The size of the cartoid artery is similar in size to the type of blood vessels which must be anastomosed in many human microsurgical procedures, such as reconstruction of an injured hand or an amputated finger or hand. This rat vessel is similar in strength and resistance to tearing to many human vessels of corresponding size, and therefore, this experiment shows that it is feasible to similarly anatomose a human vessel.

The anastomosis performed in the above Example is an end-to-end anastomosis in which a first vessel end is anastomosed to a second vessel end. Generally in such anastomosis procedures, the two vessel ends are about the same diameter. If the vessel ends are of somewhat different diameters, the ring size is selected according to the diameter of the smaller vessel and the smaller vessel end is the end drawn through and initially everted around the ring and the larger vessel end is then tented and hooked thereover. The apparatus described herein may also be used for effecting an end-to-side anastomosis in which a vessel end is drawn through, everted and hooked to the ring and then a second vessel having a prepared opening in its sidewall of a diameter generally equal to the lumen of the first vessel end is draped over the everted first vessel end and impaled on the hooking means.

Important advantages of the present invention can now be more fully appreciated. The hooking protrusions provide a very rapid means for joining a pair of blood vessels to an anastomosis ring, requiring no time-consuming suturing to be performed. The short time needed for a skilled surgeon to perform each anastomosis using the apparatus and method of the present invention can be expected to contribute greatly to the success of a microsurgical procedure. The anastomosis of a pair of vessels may be performed entirely by a single surgeon without assistance by holding the tab in one hand and a pair of surgical forceps in the other. The anastomosis is performed without clamping means that holds the vessel ends together (although clamps may be used to occlude fluid flow during the anastomosis procedure).

While the invention has been described in terms of certain preferred embodiments, modifications obvious to one with ordinary skill in the art may be made without departing from the scope of the present invention. For example, it is expected that the place of attachment to the ring of the neck extending from the tab and also the position and configuration of the notches or score lines that facilitate removal of the neck and tab may vary in different models of the device to best allow a surgeon to remove the tab, e.g., with a scissors, after anastomosis without damaging the vessels attached to the ring.

Various features of the invention are emphasized in the following claims.

What is claimed is:

1. Apparatus for anastomosing a first living vessel having a prepared end and an open first passageway therein to a second living vessel having a second passageway and a prepared opening, the apparatus comprising
a substantially encircling ring defining a plane and having protruding means at two or more locations for hooking said vessels thereon along said prepared end and said prepared opening, said ring having sufficient rigidity to act as the sole support of both vessels joined thereto and said protruding means having sufficient rigidity to retain both of said vessels hooked thereon, and
tab means attached to said ring providing for positioning of the ring during surgery, said tab means being displaced from the plane of the ring.

2. Apparatus according to claim 1 wherein said protruding means are integrally formed with said ring.

3. Apparatus according to claim 1 wherein said protruding means extend radially outward of said ring.

4. Apparatus according to claim 1 wherein the axes of said protruding means are disposed at an angle of from 0° to about 60° relative to the plane of the ring.

5. Apparatus according to claim 1 wherein the external diameter of said ring is between about 1.05 and about 1.7 times the internal diameter of said ring.

6. Apparatus according to claim 1 wherein said protruding means extend radially outward of said ring and the outer extremities of said protruding means lie along a circular locus of a diameter between about 1.8 and about 2.6 times the internal diameter of said ring.

7. Apparatus according to claim 1 wherein said tab means is integrally formed with said ring.

8. Apparatus according to claim 1 wherein said tab means is disposed at an angle relative to the plane of said ring, the angling of said tab means displacing it from the plane of the ring.

9. Apparatus according to claim 1 wherein said tab means is joined to said ring by a severable neck.

10. Apparatus according to claim 9 wherein said tab means is displaced from the plane of the ring through said severable neck.

11. Apparatus according to claim 1 wherein said tab means has an uneven surface adapted for gripping by a surgical instrument.

12. Apparatus according to claim 1 wherein said substantially encircling ring is not completely encircling, having a pair of spaced-apart ends defining a gap therebetween for accommodating connective tissue.

13. A microsurgical forceps comprising a pair of arms biased to an open position, a base end at which said tangs are joined together, said arms each having a maximum width sufficient to promote convenient gripping of the same by the surgeon, a neck portion narrowing the width of said forceps adjacent to the end opposite said base, and a tip having a width at least about 15 times less than the maximum width of said arms, each of said tips having a pair of prongs flanking a generally U-shaped opening.

14. A microsurgical forceps according to claim 13 wherein each of said arms is resiliently deformable and has a maximum thickness and each of said tips has a thickness at least about 10 times less than said maximum thickness.

15. A microsurgical forceps according to claim 13 wherein the maximum width of said tip is 0.5 mm or less.

16. A microsurgical forceps according to claim 13 wherein the maximum thickness of each of said tips is 0.1 mm or less.

17. A method of anastomosing a first living vessel having a prepared end and a first passageway therein to a second living vessel having a prepared opening communicating with a second passageway, the method comprising:
providing a substantially encircling ring having a central opening and having protrusions at two or more circumferentially spaced locations, said ring having sufficient rigidity to act as the sole support of both vessels joined thereto and said protrusions having sufficient rigidity for retaining both of said vessels hooked thereon, said ring also having preattached tab means, holding said ring by said preattached tab means and drawing the end of said first vessel through the central opening in said ring, pulling portions of the wall of said first vessel radially outward over each of said protrusions, in turn, and impaling said first vessel thereon from its outside to its intima, thereby everting the end of said first vessel, and subsequently pulling portions of the wall of said second vessel radially outward over each of said protrusions, in turn, and hooking said second vessel thereon from its intima to its outside, thereby bringing the intima of said second vessel into apposition with the intima of said everted first vessel.

18. A method according to claim 17 including the step of holding the preattached tab means at a location displaced from the plane of the ring, thereby facilitating the line of sight of impaling said vessels to said protrusions.

19. A method according to claim 17 including the step of detaching said tab means from said ring after joining said vessels thereto.

20. A method according to claim 17 wherein said ring is selected according to the external diameter of the living vessel so that its internal diameter is between about 0 and about 30 percent less than the external diameter of the end of the first vessel.

21. A method according to claim 20 wherein the external diameter of said ring is between about 5 and about 40 percent greater than the external diameter of the end of the first vessel.

22. A method of anastomosing a first vessel having a prepared end and a first passageway therein to a second living vessel having a prepared opening communicating with a second passageway, the method comprising providing a substantially encircling ring having protrusions at two or more circumferentially spaced locations, said ring having sufficient rigidity to act as the sole support of both vessels joined thereto and said protrusion having sufficient rigidity for retaining both of said vessels hooked thereon, providing a microsurgical forceps comprising a pair of tangs joined at a base end and each tang having a tip at the other end, which tips together are proportioned to fit through the opening in said ring, each of said tips having two prongs flanking a generally U-shaped opening, positioning said ring adjacent to the end of the first vessel, drawing said first vessel end through the ring, pulling with said forceps a portion of the wall of said first vessel radially outward, positioning the aligned U-shaped openings of the forceps tips with the outer extremity of one or said protrusions and impaling said first vessel end so that said prongs flank said protrusion, and then sliding said forceps away from said protrusion leaving said vessel wall portion impaled thereon, in a similar manner pulling other portions of the wall of said first vessel and impaling the same on the other protrusions, and then in a similar manner pulling portions of the wall of the second vessel and hooking the same on each of said protrusions, in turn, thereby apposing the two vessels and anastomosing the same together.

* * * * *